US00PP26076P3

(12) United States Plant Patent
Shipley

(10) Patent No.: US PP26,076 P3
(45) Date of Patent: Nov. 10, 2015

(54) ***SALVIA GREGGII* PLANT NAMED 'RUBY SLIPPERS'**

(50) Latin Name: *Salvia greggii*
Varietal Denomination: Ruby Slippers

(71) Applicant: Nicholas Benoit Shipley, Tucson, AZ (US)

(72) Inventor: Nicholas Benoit Shipley, Tucson, AZ (US)

( * ) Notice: Subject to any disclaimer, the term of this patent is extended or adjusted under 35 U.S.C. 154(b) by 113 days.

(21) Appl. No.: 13/987,784

(22) Filed: Sep. 3, 2013

(65) Prior Publication Data
US 2015/0067939 P1 Mar. 5, 2015

(51) Int. Cl.
*A01H 5/02* (2006.01)

(52) U.S. Cl.
USPC ..... Plt./475
CPC ..... *A01H 5/02* (2013.01)

(58) Field of Classification Search
USPC ..... Plt./475
See application file for complete search history.

*Primary Examiner* — Keith O. Robinson

(57) ABSTRACT

A new and distinct *Salvia greggii* plant named 'Ruby Slippers' is characterized by vivid red flowers, compact form, long bloom period and high tolerance to desert heat.

2 Drawing Sheets

Latin name: *Salvia greggii.*
Varietal denomination: Ruby Slippers.

BACKGROUND OF THE INVENTION

*Salvia greggii*, a member of the plant family Lamiaceae, is native to central and southwest Texas and south through the highlands of the Chihuahuan Desert in Mexico. *Salvia greggii*, which is also known as Autumn Sage, produces shrubby growth, ultimately reaching 1-3 ft tall×2-4 feet wide. Plants flower almost year around in mild climates, producing ¼-1 inch long tubular flowers which attract hummingbirds. Flower color varies from the typical reds found in the wild to white, pink, yellow and shades of purple in cultivated varieties.

Autumn sage has been cultivated in Texas as early as 1885, becoming popular in the southwestern United States as a landscape shrub about 85 years later and subsequently as a landscape shrub and as an annual flowering bedding plant worldwide. Many cultivars and hybrids have been produced, many including parentage from the closely related *Salvia microphylla*, which has a much larger adaptational range as well as more variability as a species.

The present invention relates to a new and distinct cultivar of *Salvia greggii* named 'Ruby Slippers'. The cultivar originated as a seedling selection from offspring of the unpatented cultivar 'Lipstick' planted in 2008. The resulting plant has a different colored flower from its parent, as well as improved heat tolerance and a more compact growth form and is the object of this application.

SUMMARY OF THE INVENTION

Among the features that distinguish the new *Salvia greggii* cultivar from all other available and commercial varieties of *Salvia greggii* known to the inventor is the following combination of characteristics: compact form, long bloom season, heat tolerance exceeding that of the unpatented cultivar 'Lipstick' and vivid red (overall) flowers 5th edition Royal Horticultural Society 2007 (R.H.S.) (50A-B).

Mature plants reach about 2.5 feet high by 3.5 feet wide. Flowers are produced in pairs on terminal spikate racemes.

The propagation procedure is as follows: Softwood cuttings containing one node with leaves and about 3" long are prepared and wetted with Dip & Grow™, a commercial auxin type plant growth hormone preparation, planted in a peat potting medium in a misting greenhouse with bottom heat in the cool season. During the warm season bottom heat is not needed. Cuttings become rooted within 3-4 weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Salvia greggii* 'Ruby Slippers' growing near Tucson, Ariz., depicted in color as nearly correct as it is possible to make in a color illustration of the character.

DETAILED PLANT DESCRIPTION

Figure 1:
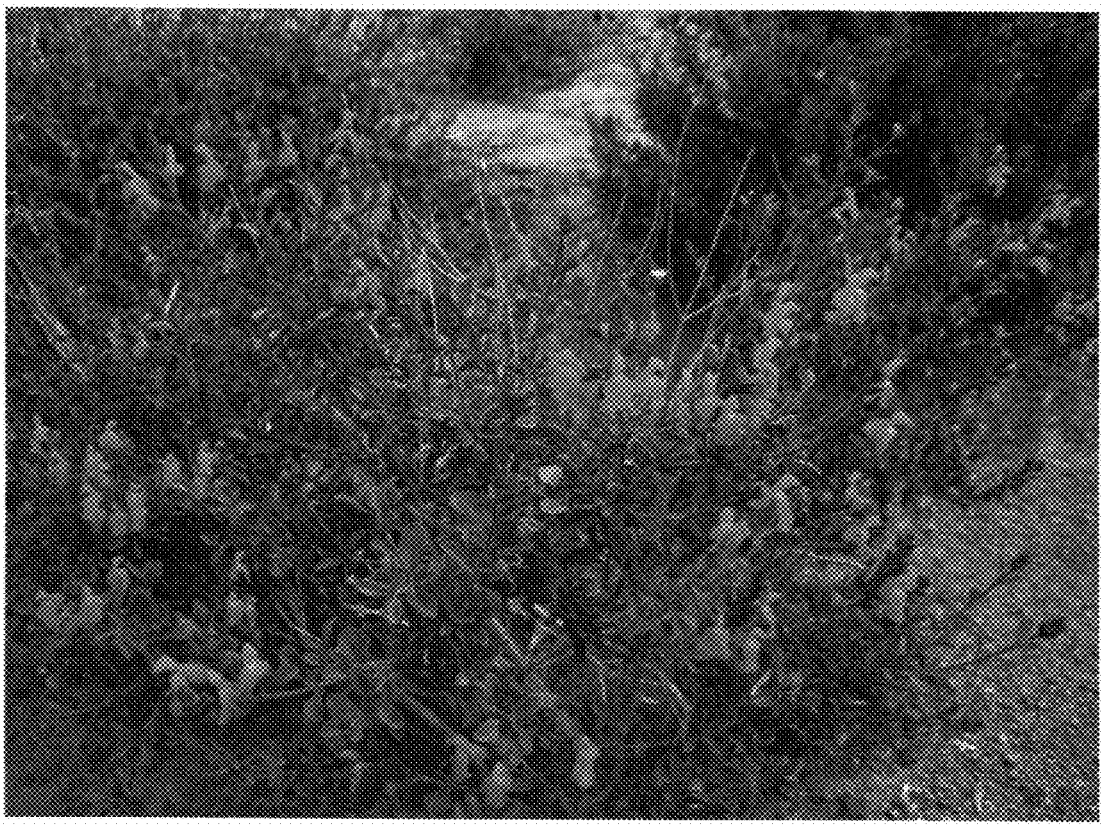
FIG. 1 illustrates a typical *Salvia greggii* 'Ruby Slippers' at about age 2 years.
Figure 2:
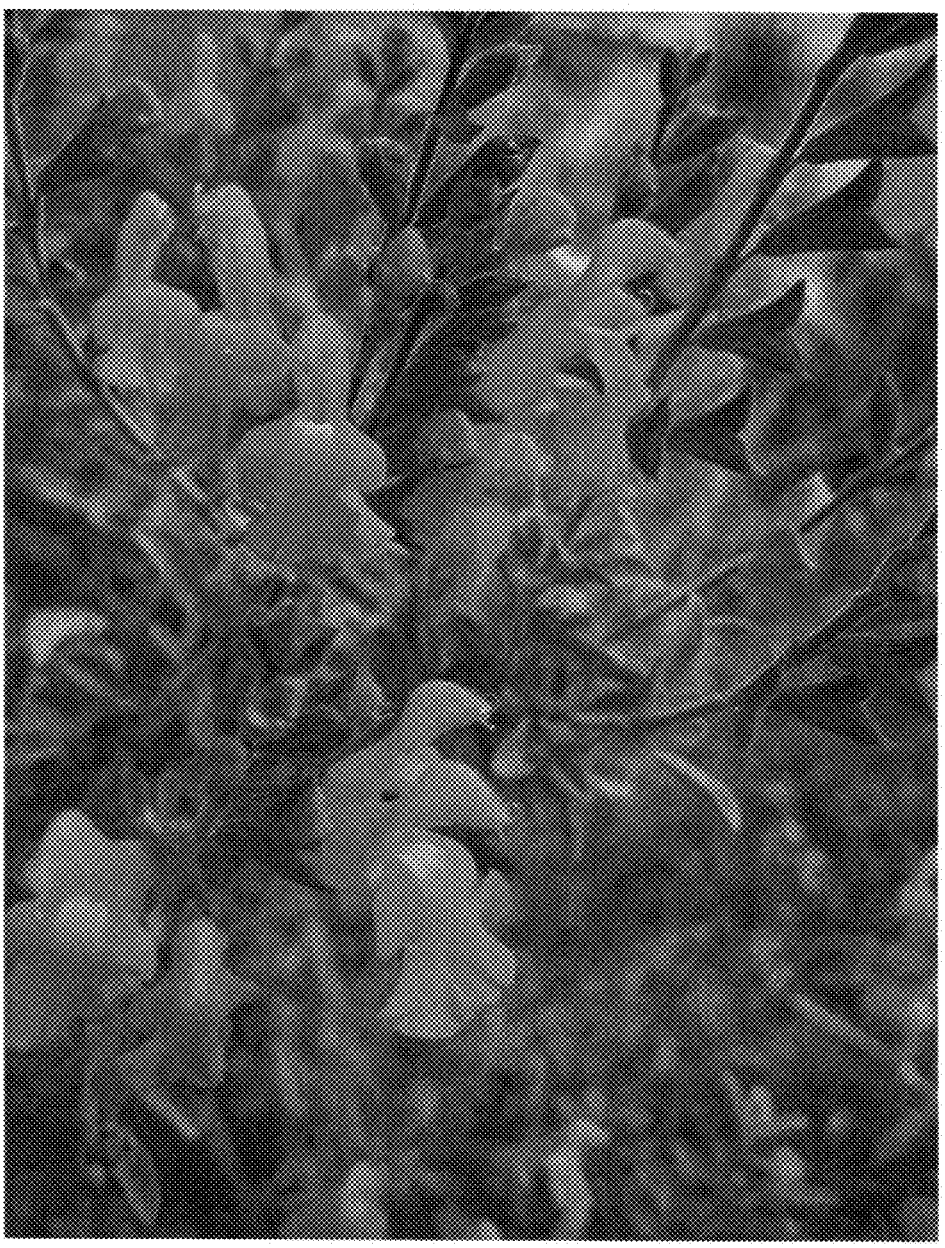
FIG. 2 shows a closeup of *Salvia greggii* 'Ruby Slippers' inflorescences and flowers.

The following plant measurements were taken from 3, 5 gallon container grown specimens approximately 1 year in age from cutting. Mature plants were also available for measurement. The color descriptions are based upon the 5$^{th}$ edition R.H.S. Colour Chart 2007. Color names other than common usage are as listed in *COLOR Universal Language and Dictionary of Names*, by Kenneth L. Kelly and Deane B. Judd; National Bureau of Standards special publication 440.

Washington, D.C.: U.S. Department of Commerce, National Bureau of Standards, December 1976.

*Salvia greggii* 'Ruby Slippers' is a highly branched, suffrutescent shrub which grows to about 2.5 feet tall by 3.5 feet wide. Stems are 14-31 cm in length, strong but brittle, especially at the bases. The stems are squarish, tapering in diameter from 2.0 mm distally to 2.5 mm basally, the surface finely puberulent, the hairs caducous with age. Stem color 138B with barely visible striations terminally to being striped with 59A basally. Stems become woody and thicken with age to a more cylindrical shape and a relatively uniform 164D color. The older stems have papery, peeling bark. Older stems range from about 2.5-15 mm in diameter, thickening with age. Primary lateral branches 6-12 cm in length, finely puberulent, suffrutescent, weaker than primary branches. Color of primary lateral branches are the same as stems. Diameter of primary lateral branches taper from 1.0-1.5 mm distally to 1.5-2.0 mm basally. Lateral branches number from 0-11 per stem. Internodes vary from 1-42 mm long, with paired, opposite leaves at the nodes. Branch angles vary from 35-45 degrees.

Leaves (color closest to 138A on both adaxial and abaxial surfaces) are opposite, and ovate/elliptical in shape, leaf base acute, apex rounded to obtuse. Leaf margins are entire basally, crenulate/denticulate apically. Leaf surface is adaxially lustrous, glabrous; abaxially less lustrous, glabrous. Leaf size is highly variable, from 4 mm wide×11 mm long up to 17 mm wide×27 mm long. Leaf veins are obscure and pinnate, slightly lighter than the surrounding leaf tissue, color 138B. Petioles range in length from 3-10 mm long, diameter 1.0-1.5 mm, more or less half cylindrical in shape, the flat side held adaxially, color adaxially 138A, abaxially 138B. Surface is finely and sparsely puberulent. Petioles are not strong, breaking squarely.

Inflorescences are produced terminally, forming a square stemmed spikate raceme, axis color distally in area of flowering 59A, basally post flowering changing to 138B. The surface of the inflorescence axis is puberulent. Inflorescences grow from 12-26 cm long including the peduncle, with up to approximately 15-20 nodes each. Peduncles measure 15-30 mm long, square in cross section, diameter 1.5-2.5 mm, color 138A, puberulent, strong. Floral bracts are carinate, 3-3.5 mm wide×5-7 mm long, ovate, apiculate, somewhat paleaceous and caducous several days before anthesis. Bract adaxial surface is glabrous, abaxial surface hispidulous. Bracts are striate, 7 nerved, the nerves and apex color 59A, basally 142D. Much of the internerval area is colored 141D, but the colors generally vary somewhat with growth conditions. Flowers are paired and opposite on the inflorescence.

Pedicles are terete, 3-4 mm long×0.5 mm in diameter. Pedicel color ranges from 60B near the floral attachment to 142B at the base. Pedicel surface is sparsely puberulent. Pedicels are weak and brittle, breaking squarely.

Buds measure 17 mm long×3.5 mm wide×5 mm high at maturity. Surface is puberulent except for the apex, which is pilose. Color of bud is 50B except at the apex, which is 50A. Bud is irregulary oblanceoloid in shape, indented on the abaxial (lower) surface.

Flowers produced are typically 29 mm long×18 mm high× 15-16 mm wide, tubular, bilabiate, ventricose with an overall color of 50A-B, the color lighter at the throat 50C. The upper lip is 10 mm long×4 mm high×4 mm wide, hooded, the anterior portion covered with pilose hairs (the hairs colored 50A), basally glabrous, color 50A-B the stigma and stamens exserted from the tip. The interior (adaxial) upper lip is glabrous, 50D. The lower lip is spreading and somewhat reflexed, glabrous, more or less 4 lobed, entire and somewhat crisped, 12 mm high×15-16 mm wide, color 50A-50B with specular spotting, lighter near the throat 50D. The abaxial lower lip is glabrous 50A-B, grading to color 50D at the throat. The glabrous floral tube reaches 19 mm long and is grooved. The pistil is about 24 mm long, the naked ovary 4 lobed, the lobes ovoid, 1 mm long×0.5 mm wide, color 1C or lighter attached to an expanded spheroidal receptacle, 1 mm diameter, color 1C or lighter. The stigma is unequally divided, the lobes parting dorsally, the upper 2.5 mm long, the lower 1 mm long, both narrowly acute, color 50A. A beard extends basally from about the midpoint of the upper lobe toward and below the fork about 4 mm. The combined stigma and style reach about 23 mm long the style elliptical, laterally compressed, 0.75 mm high×0.25 mm wide in cross section. The style color grades from that of the stigma basally to 50D or lighter. The 2 stamens are paired and epipetalous, the filaments fused at the attachment, then forming a united, detached, basal extension that forms a teeter totter like device that tips apically downward when a hummingbird inserts it bill into the tube, placing pollen on the bird's bill to pollinate the next flower. The forward portion of the filament measures 5 mm long×0.8 mm in diameter, tapering to the anther. The portion below the attachment measures 7 mm long×0.8 mm in diameter. The filaments are lighter than 50D. The dehisced anthers are basifixed, 2 mm long×1 mm thick, the pollen colored 26B.

The fused calyx (sepals) is bilabiate, laterally compressed, at anthesis measuring 11 mm long×7 mm high×2.5 mm wide, striped and ridged, the ridges 59A, the valleys 143B, the exterior surface puberulent, interior glabrous. Apex of upper lobe is apiculate, acute; the lower lobe is acutely divided, 2 lobed, both lobes apiculate, the lobes unequally acute. Calyx margin is entire except for the lobes, finely puberulent.

Fecundity is highly variable with conditions and pollination with from 0 to 3 seeds being produced from each flower, more typically from 0 to 2 seeds. Seeds (nutlets) are obovoid, lustrous, black (203B), laterally compressed, measuring from 3.1-3.6 mm in length by 1.0 to 1.4 mm in width by 1.4-2.0 mm in height. Seed scar is slightly depressed, offset laterally towards the axis of the pedicel, more or less elliptical in shape appearing as two circles contacting each other with the axis of the two circles aligned with the lateral axis of the seed. The seed scar is color N199A on the circles while the centers have the same color as the seed surface (203B).

Flowering is nearly year round under favorable conditions of temperature and moisture, but heaviest from March to May and September through October under conditions prevailing in Tucson, Ariz. Flowers last 2-4 days, the corolla becoming deciduous. The plant described had 50 flowers present at the time of description.

*Salvia* 'Ruby Slippers' is adapted to USDA hardiness zones 7-10, specifically tolerating temperatures from at least 0-120 degrees Fahrenheit. 'Ruby Slippers' has proven to be among the most heat tolerant *Salvia greggii* cultivars, surviving in the nursery when most other commercially available cultivars die.

Plants exhibit a moderate growth rate, reaching mature size under favorable growing conditions within 3 years.

No diseases or harmful insects were noted on observed specimens.

COMPARISONS TO RELATED *SALVIA GREGGII*

Compared to its female parent, 'Lipstick', 'Ruby Slippers' is considerably more heat tolerant, more compact, with the flower throat less white than that of 'Lipstick', which has a very white throat. The seeds were the result of open pollination such that the male parent (which could also be a self) is unknown.

'Ruby Slippers' may be most easily distinguished from other cultivars by the character of its flowers, in particular flower color. The color of 'Ruby Slippers' flowers varies from 50A-B, while 'Ultra Violet' has flowers with a mix of 83A, N81A, 77A and N155A; flowers of 'Icing Sugar' have a mix of N74B, 68A, 76C and 73A; flowers of 'Flosalg02' vary from 4B-D.

I claim:

1. A new and distinct *Salvia greggii* plant substantially as described and illustrated herein.

* * * * *